(12) United States Patent
Abdelsalam et al.

(10) Patent No.: US 11,446,648 B2
(45) Date of Patent: Sep. 20, 2022

(54) PORPHYRIN-BASED CATALYSTS FOR WATER SPLITTING

(71) Applicant: KING FAISAL UNIVERSITY, Al-Ahsa (SA)

(72) Inventors: Mamdouh E. Abdelsalam, Bristol (GB); Ibrahim A. Elghamry, Cairo (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 662 days.

(21) Appl. No.: 16/279,979

(22) Filed: Feb. 19, 2019

(65) Prior Publication Data

US 2020/0261897 A1    Aug. 20, 2020

(51) Int. Cl.
| | | |
|---|---|---|
| *C07D 487/22* | (2006.01) | |
| *B01J 31/18* | (2006.01) | |
| *H01M 4/62* | (2006.01) | |
| *H01M 4/90* | (2006.01) | |
| *B01J 20/34* | (2006.01) | |

(52) U.S. Cl.
CPC .......... *B01J 31/183* (2013.01); *C07D 487/22* (2013.01); *H01M 4/623* (2013.01); *H01M 4/9008* (2013.01); *H01M 4/9083* (2013.01); *B01J 20/3441* (2013.01); *B01J 2231/62* (2013.01); *B01J 2531/004* (2013.01); *B01J 2531/005* (2013.01); *B01J 2531/025* (2013.01); *B01J 2531/845* (2013.01)

(58) Field of Classification Search
None
See application file for complete search history.

(56) References Cited

U.S. PATENT DOCUMENTS

| | | |
|---|---|---|
| 7,037,414 B2 | 5/2006 | Fan |
| 9,205,420 B2 | 12/2015 | Reece et al. |
| 9,459,545 B2 | 10/2016 | Tanaka et al. |
| 2014/0061063 A1 | 3/2014 | Yuasa et al. |

FOREIGN PATENT DOCUMENTS

WO    2010088723 A1    8/2010

OTHER PUBLICATIONS

Ghazzali et al., "Synthesis, EPR and DFT calculations of rare Ag(II)porphyrins and the crystal structure of [Zn(II) tetrakis(4-bromo-2-thiophene)porphyrin]," Inorganic Chemistry Communications, 11:9, 2008, pp. 1019-1022.

Friedlein et al., "Solution-processed, highly oriented supramolecular architectures of functionalized porphyrins with extended electronic states," Chemical Communications, 15, 2005, pp. 1974-1976.

(Continued)

*Primary Examiner* — Yun Qian
(74) *Attorney, Agent, or Firm* — Nath, Goldberg & Meyer; Richard C. Litman

(57) ABSTRACT

The porphyrin-based catalysts for water splitting are composites of porphyrin or metalloporphyrin active ingredients, conductive carbon (e.g., graphene sheets, vapor grown carbon fiber, carbon black, etc.), and a polymer or binder that may be coated on a glassy carbon electrode. The polymer or binder may be Nafion oil or polyvinylidine difluoride. The porphyrin may be a porphyrin having a transition metal or hydrogen at its center, and may be halogenated and/or have a thiophene substituent.

4 Claims, 4 Drawing Sheets

(56) References Cited

OTHER PUBLICATIONS

Kellett et al., "Cobalt(I) porphyrin catalysts of hydrogen production from water", Inorganic Chemistry (1985), vol. 24, No. 15, pp. 2373-2377 (Abstract only).

Jia et al., "Pyrolyzed cobalt porphyrin-based conjugated mesoporous polymers as bifunctional catalysts for hydrogen production and oxygen evolution in water", Chemical Communications (2016), vol. 52, pp. 13483-13486 (Abstract only).

Downes et al., "Electrocatalytic Metal-Organic Frameworks for Energy Applications", ChemSumChem (2017), vol. 10, pp. 4374-4392.

PORPHYRIN-BASED CATALYSTS FOR WATER SPLITTING

BACKGROUND

1. Field

The disclosure of the present patent application relates to catalysts for oxygen evolution reactions, and particularly to porphyrin-based catalysts for water splitting that can be used for electrolysis in connection with renewable energy sources, such as fuel cells.

2. Description of the Related Art

The search for renewable energy sources to lessen reliance on the depleting supply of fossil fuel has led researchers to focus a considerable amount of attention on the conversion and storage of renewable energy stored in chemical bonds. Splitting water into hydrogen and oxygen is regarded as a potentially attractive source of hydrogen, which can be stored and converted into electricity in fuel cells. The water splitting process involves two half reactions, including:

$$2H_2O \leftrightarrows O_2 4H^+ + 4e^- (V_{anode} = 1.23 \, V\text{vs.} NHE) \quad (1)$$

$$4H^+ + 4e^- \leftrightarrows 2H_2 (V_{cathode} = 0.0 \, V\text{vs.} NHE) \quad (2)$$

where NHE is the normal hydrogen electrode. Equation (1) is the oxygen evolution reaction (OER), which takes place at the anode. Equation (2) is the hydrogen evolution reaction (HER), which takes place at the cathode. The reverse of Equation (1) is the oxygen reduction reaction (ORR), which takes place at the cathode of some fuel cells.

The water splitting process is an endothermic reaction, which requires the input of energy to move forward. The OER is a four electron-four proton process involving the formation of a rigid O—O bond, and is the rate-limiting step in the water splitting process. Catalysts have been developed to reduce the energy barrier for the OER to improve the efficiency of the water splitting process. However, the noble metal and transition metal oxide catalysts currently available are expensive and suffer from low efficiency and instability, particularly in acidic media, rendering the current catalysts commercially infeasible.

Thus, porphyrin-based catalysts for water splitting solving the aforementioned problems are desired.

SUMMARY

The porphyrin-based catalysts for water splitting are composites of porphyrin or metalloporphyrin active ingredients, conductive carbon (e.g., graphene sheets, vapor grown carbon fiber, carbon nanotube, carbon black, etc.), and a polymer binder that may be coated on a glassy carbon electrode. The polymer binder may be Nafion oil or polyvinylidine difluoride. The porphyrin may be a porphyrin having a transition metal or hydrogen at its center, and may be halogenated and/or have a thiophene substituent. In a preferred embodiment, the porphyrin has the structure:

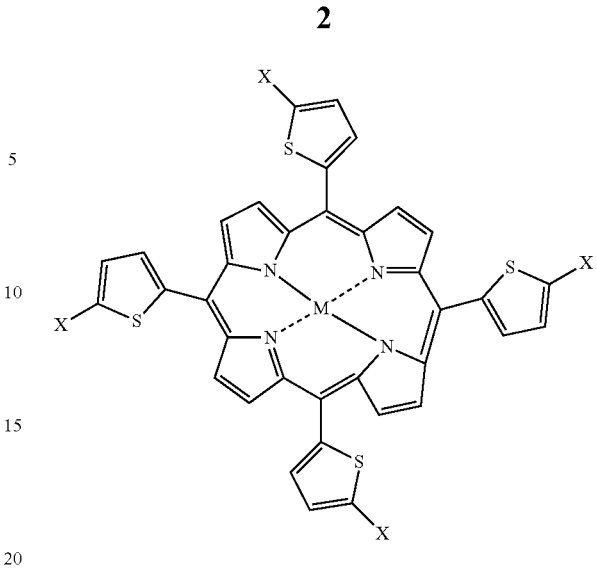

wherein M is $H_2$, CO, Ni, Cu, or Zn, and X is F, Cl, or Br.

Porphyrins exhibiting absorption at the red end of the visible light spectrum and near infrared spectrum are predicted to have high electronic conductivity and good electrocatalytic activity. This type of porphyrin may be synthesized by extending the pi-electron system of the main porphyrin ring, by introducing an aromatic moiety (e.g., phenyls, thienyls, etc.) at the meso-position(s). Porphyrins with five-membered thienyls at the meso-positions have increased red-shift effect when compared to porphyrins substituted by six-membered phenyls. Thus, the porphyrin-based catalysts for water splitting of the present disclosure should demonstrate higher electronic conductivity than meso-tetraphenylporphyrins.

The pi-electron system of thienyl substituents at the meso-positions, which are bonded directly to the core porphyrin, have electronic first-order effects on the spectroscopic properties (e.g., absorption and emission) of the porphyrin ring. The peripheral substituents on the thienyl ring (x=F, Cl, or Br) have electronic second order effects, and thus the halogen substituents are less important in improving water splitting efficiency of the porphyrin-based catalysts for water splitting.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
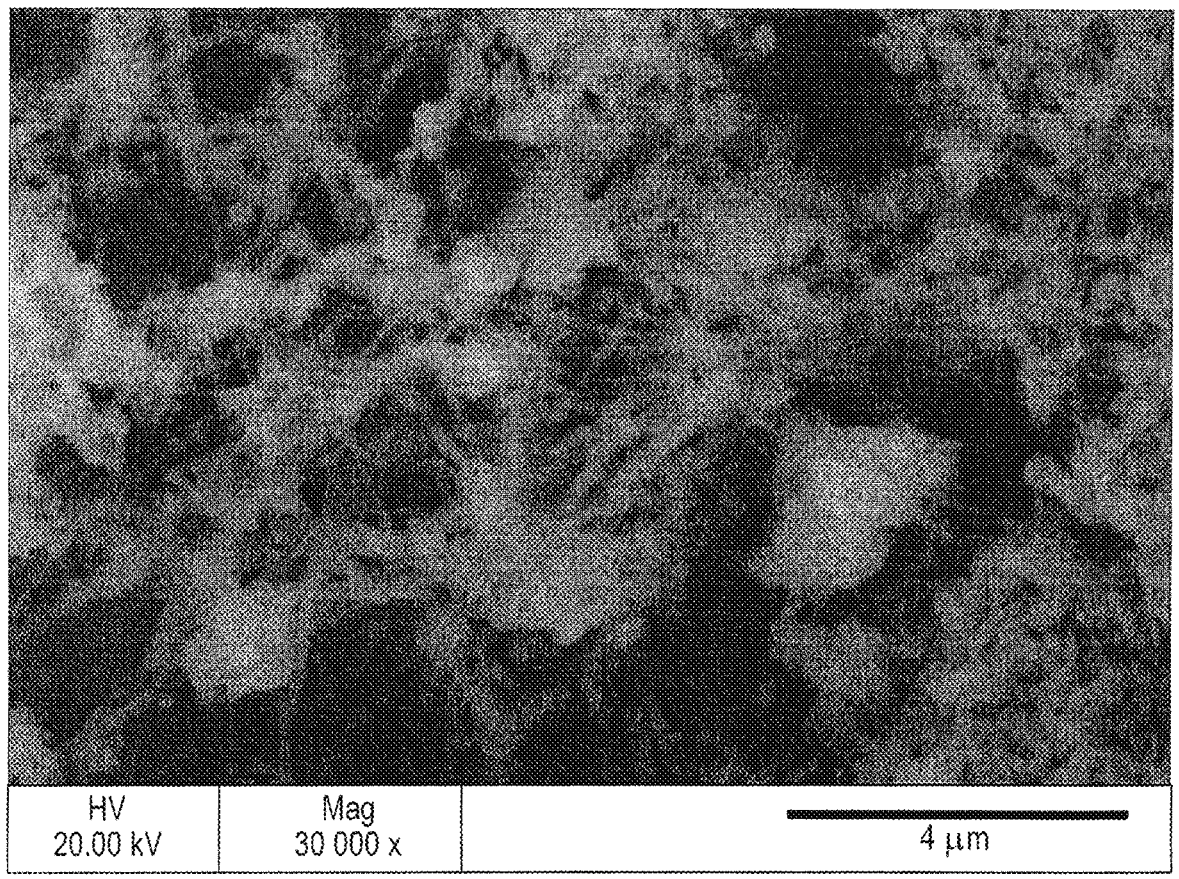
FIG. 1 depicts a scanning electron micrograph (SEM) of an exemplary porphyrin-based catalyst for water splitting comprising 50 wt % 5,10,15,20 tetrakis (5-bromothiophen-2-yl) porphyrin, 40 wt % vapor grown carbon fiber (VGCF) and 10 wt % Nafion oil.

The porphyrin-based catalysts for water splitting are composites of porphyrin or metalloporphyrin active ingredients, conductive carbon (e.g., graphene sheets, vapor grown carbon fiber, carbon nanotube, carbon black, etc.), and a polymer or binder that may be coated on a glassy carbon electrode. The polymer binder may be Nafion oil or polyvinylidine difluoride (PVDF). The porphyrin may be a porphyrin having a transition metal or hydrogen at its center, and may be halogenated and/or have a thiophene substituent. In a preferred embodiment, the porphyrin has the structure:

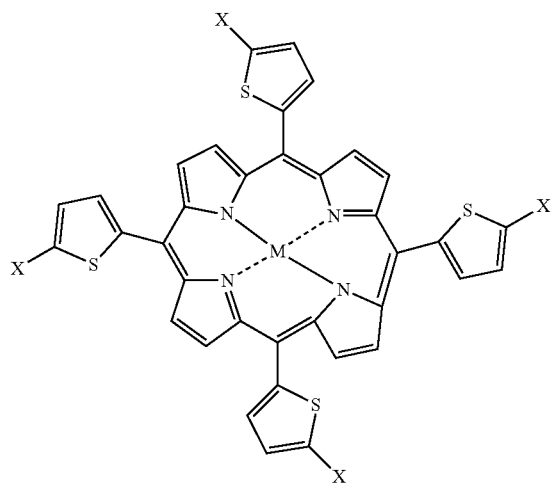

wherein M is $H_2$, Co, Ni, Cu, or Zn, and X is F, Cl, or Br.

The catalysts are composites comprising porphyrin powder, carbon conductive materials, and polymer solution. The porphyrin has extraordinary catalytic activity towards the oxygen evolution reaction, while the conductive carbon additives provide an enhanced electrical conductivity, which is essentially required to catalyze the water splitting reaction. Additionally, the polymer will contribute in improving the mechanical integrity of the catalyst. Combining the unique properties of the components of the composite catalyst has significantly reduced the energy required to perform the water splitting process, and hence, improved the efficiency of oxygen gas production. Also, the porphyrin-based catalyst is very stable and uniquely catalyzes the oxygen evolution reaction in acidic, neutral and basic media. Additionally, flexibility of the organic porphyrin molecules and carbon network has contributed in improving the stability of the catalyst. Moreover, the catalysts are based on low cost carbon materials and scalable, synthesizable porphyrins, which make the catalysts a very cost effective technology for producing clean, renewable energy.

EXAMPLE 1

Synthesis of Porphyrin Catalysts

The targeted-porphyrins may be prepared using a one-pot, multi-step approach. Generally, a mixture of equimolar quantity of pyrrole and selected aldehydes in dimethylformamide (DMF) was heated at 100° C. under argon atmosphere. Then, a similar molar quantity of p-toluenesulfonic acid (PTSA) was added, and the reaction mixture was heated up gradually to 140° C. and kept at this temperature for one hour. The obtained dark violet solution was left to cool to room temperature. Then the dark violet solution was poured into cooled water/triethylamine (TEA) (5%) and left for 30 min. with stirring. The resulting solid precipitate was filtered, washed several times with water, air dried and purified by column chromatography ($CHCl_3$/MeOH 99:1 v/v) and crystallization from $CHCl_3$/MeOH. The resulting porphyrins may then be reacted with a metal acetate to produce a desired metallo-porphyrin complex as follows: a mixture of the free base porphyrin (1 mole) and metal acetate (3 moles of cobalt acetate, nickel acetate, copper acetate, or zinc acetate) is dissolved in dimethylformamide (DMF). The reaction mixture is heated and kept at 120° C. under argon atmosphere for 3 hours, left to cool, and poured into cool water. The solid product is collected by filtration, washed with water several times, air dried, and purified by column chromatography ($CHCl_3$/MeOH 99:1 v/v) and crystallization from $CHCl_3$/MeOH.

A preferred structure of the porphyrins is:

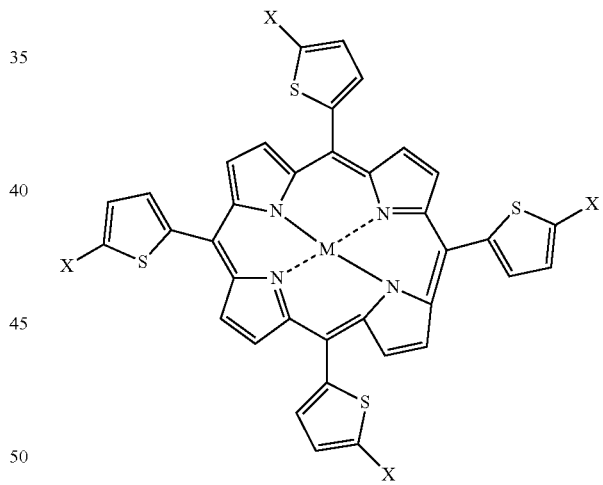

wherein M is $H_2$, Co, Ni, Cu, or Zn, and X is F, Cl, or Br.

Composite electrodes with the porphyrin-based catalysts may be made by dispersing a conductive carbon in an organic solvent (e.g., methanol, ethanol, propanol or mixtures thereof) to form a first reaction mixture, mixing the porphyrin complexes with the first reaction mixture to form a second reaction mixture, adding a polymer solution (e.g., Nafion oil, PVDF, etc.) to the second reaction mixture to produce a third reaction mixture (a thick, homogenous ink), and coating the third reaction mixture (between 100 and 200 µl) directly on a conducting substrate (e.g. a glassy carbon electrode), which is baked in a drying oven at 80° C. for ten minutes, thereby producing a composite electrode with a porphyrin-based catalyst. Each reaction mixture may be mixed using an ultrasonic probe for about an hour.

The weight percentage of the porphyrin compound, conductive carbon, and polymer used to form the composite electrode may vary, exemplary weight percentages being listed in Table 1.

TABLE 1

Exemplary Composition of Porphyrin-Based Catalyst by Weight Percent

| Porphyrin | Conductive Carbon | Polymer |
|---|---|---|
| 80 | 10 | 10 |
| 70 | 20 | 10 |
| 60 | 30 | 10 |
| 50 | 40 | 10 |

Exemplary porphyrin-based catalysts were made as described above. FIG. 1 shows a SEM micrograph of one such catalyst [50 wt % 5,10,15,20 tetrakis (5-bromothiophen-2-yl) porphyrin, 40 wt % vapor grown carbon fiber (VGCF) and 10 wt % Nafion oil]. In the micrograph, the carbon fibers can be easily recognized, while the porphyrin particles are visible as less dark particles physically attached to the fibers. The fibrous nature of the VGCF is also apparent, and the uniform distribution of the porphyrin-based catalyst throughout the VGCR carbon network is confirmed.

Exemplary composite electrodes were made with the porphyrin-based catalysts and tested as follows. Performance of the electrocatalysts was evaluated by measuring overpotential ($\eta$), the difference between the applied potential (E) and the potential under equilibrium conditions ($E_{eq}$). A low $\eta$ was indicative of improved catalytic performance.

The rate of oxygen evolution reaction was calculated using the Tafel equation, correlating the rate of the electrochemical reaction and the overpotential according to Equation 3:

$$\log(i) = \log(i_0) + \frac{\eta}{b}, \quad (3)$$

where i is the current density, $i_o$ is the exchange current density (i.e., the current at zero potential), and b is the Tafel slope. The magnitude of the exchange current density ($i_o$) reflects the intrinsic bonding/charge transferring interaction between the electrocatalyst and the reactant. A high exchange current density was used as an indicator of a suitable catalyst for the reaction being tested.

Tafel slopes were also calculated by plotting log(i) versus $\eta$, producing lines with a slope of b. A small Tafel slope indicates that current density will increase significantly with little change in overpotential, thus indicating a faster reaction rate for oxygen evolution. Thus, small Tafel slopes were used as indicators of better performing electrocatalysts. Tafel slopes were calculated according to Equation 4:

$$b = \frac{\partial \eta}{\partial \log i}. \quad (4)$$

For this example, four different composite electrodes were tested, including a bare glassy carbon electrode (GC), a GC electrode coated with 90 wt % vapor grown carbon fiber and 10 wt % Nafion (VGCF), a glassy carbon electrode coated with 90 wt % cobalt-porphyrin compound and 10 wt % Nafion (CoP) (but no conductive carbon), and a glassy carbon electrode coated with 50 wt % cobalt-porphyrin compound, 10 wt % Nafion, and 40 wt % VGCF (CoP-VGCF). The weight load of the coated electrodes was 1 mg/cm$^2$.

Figure 2:
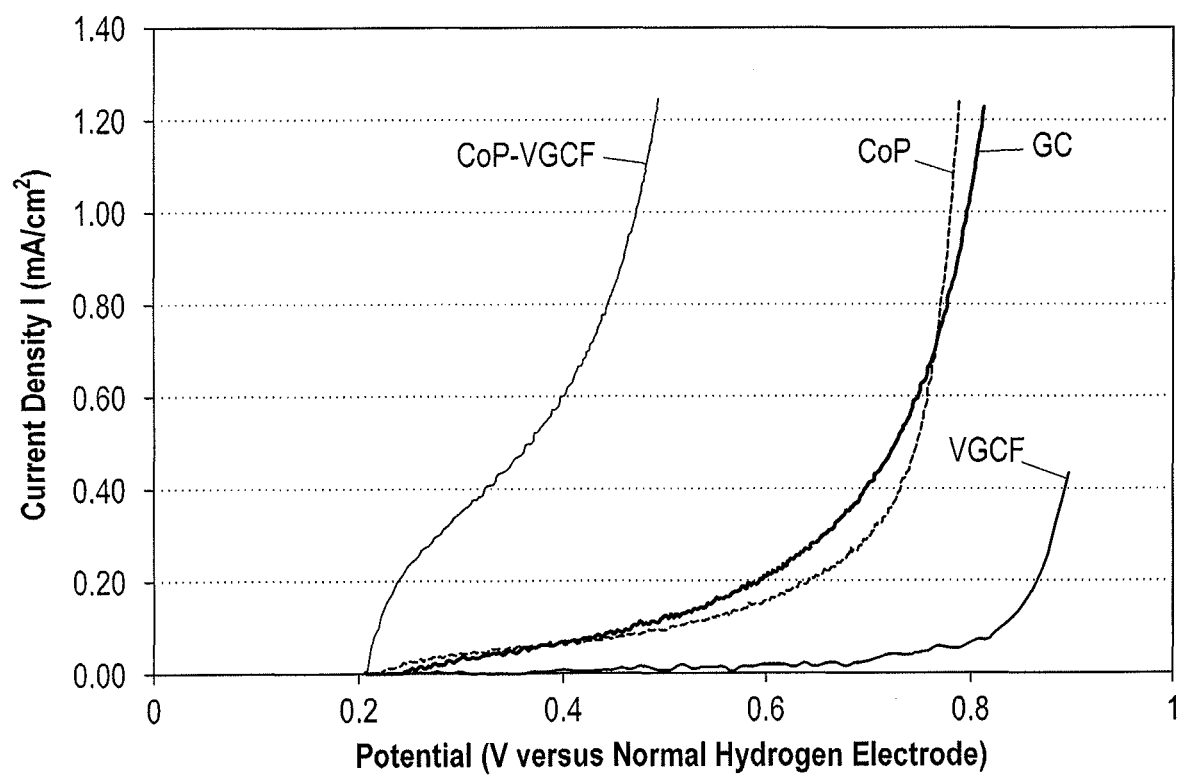
FIG. 2 depicts a comparison of linear sweep voltammograms of various electrodes in an aqueous alkaline media containing 1 mol. Liter of sodium hydroxide (NaOH), including a glassy carbon electrode (GC), a glassy carbon electrode coated with 90 wt % VGCF and 10 wt % Nafion (VGCF), a glassy carbon electrode coated with a cobalt-porphyrin slurry 90 wt % with 10 wt % Nafion (CoP), and a glassy carbon electrode coated with a composite including 50 wt % of a cobalt-porphyrin, 10 wt % Nafion, and 40 wt % vapor grown carbon fiber (CoP-VGCF), showing current density as a function of potential vs. a normal hydrogen electrode.
Figure 3:
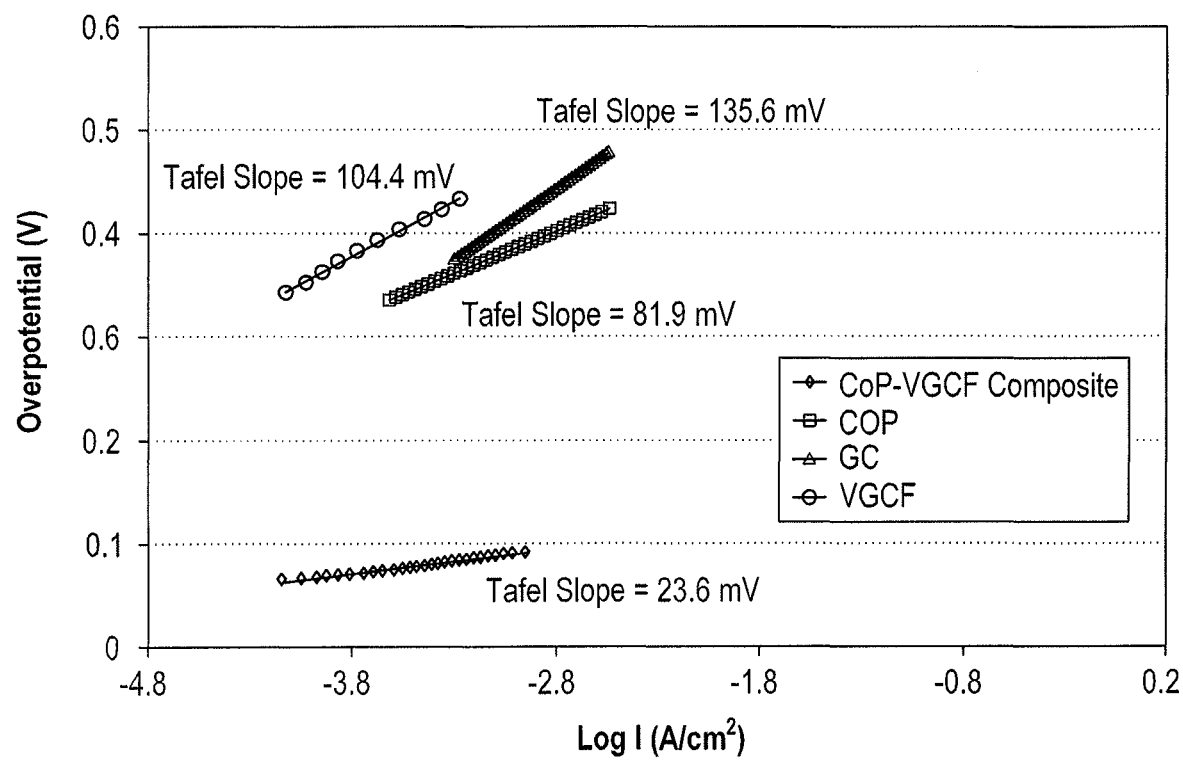
FIG. 3 depicts Tafel plots corresponding to the linear sweep voltammograms of FIG. 2.

FIG. 2 depicts linear sweep voltammograms recorded in 1 M NaOH solution at a scan rate of 100 mV/s for all four tested electrodes. Electrochemical measurements were performed using an Ezstat potentiostat/galvanostat supported with EZware software. Electrochemical measurements were carried out in a conventional three-electrode cell. A glassy carbon base electrode coated with 2 mg cm$^{-2}$ of the porphyrin-based catalyst was used as a working electrode. The counter electrode was made of a platinum mesh (area 1 cm$^2$). The reference electrode was Ag/AgCl/KCL (sat.). The potential was measured against the Ag/AgCl/KCl (Sat.) electrode, then converted to a normal hydrogen electrode by adding 0.197 V. The resulting voltammograms illustrate the low potential required for the CoP-VGCF composite catalyst to catalyze the oxygen evolution reaction. Tafel plots of the results shown in FIG. 2 are depicted in FIG. 3, demonstrating the significantly reduced Tafel slope of the CoP-VCGF electrode when compared with the other tested electrodes.

The following examples illustrate the present teachings

EXAMPLE 2

Fabricating 5,10,15,20 Tetrakis (5-bromothiophen-2-yl) Cobalt Porphyrin Electrode A porphyrin-based catalyst for water splitting was fabricated having 50 wt % cobalt porphyrin complex, 40 wt % VGCF, and 10 wt % Nafion oil. First, 0.4 g of VGCF was dispersed in 2 ml methanol in an ultrasonic bath for an hour. Then 0.5 g cobalt-porphyrin complex were added in the ultrasonic bath for a further hour. A further 2 g of Nafion oil polymer solution (5 wt %) was added to the mixture, producing a thick homogenous ink. This mixture was then mixed in an ultrasonic bath for a further hour. The resulting ink was stable and homogenous. A volume of between 100 and 200 µl of the ink was coated directly onto the surface of a glass carbon electrode (2 mm diameter) and the electrode was transferred to a drying oven and baked at 80° C. for 10 minutes.

Figure 4:
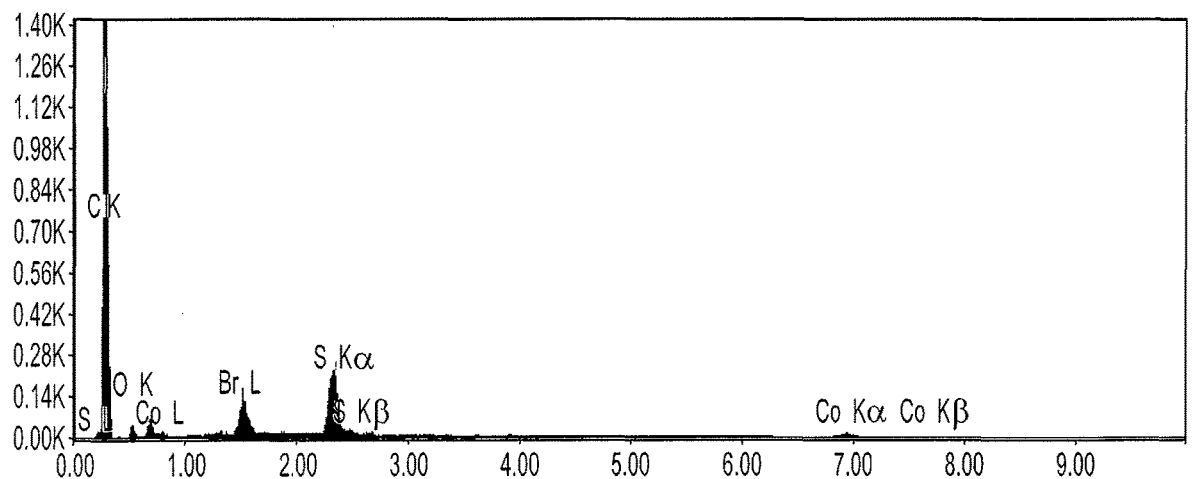
FIG. 4 depicts an energy-dispersive X-ray spectrograph of a porphyrin-based catalyst for water splitting.

A scanning electron micrograph of this composite electrode is depicted in FIG. 1, illustrating the fibrous nature of the VCGF and confirming that the cobalt porphyrin catalyst is uniformly distributed on the VGCF carbon network. These results were also confirmed by Energy-Dispersive X-ray Spectroscopy (EDX). (See FIG. 4 and Table 2)

TABLE 2

EDX of cobalt-porphyrin composite

| Element | Weight % | Atomic % | Net Int. | Error % |
|---|---|---|---|---|
| CK | 89.2 | 93.05 | 187.29 | 6.06 |
| OK | 7.41 | 5.8 | 6.61 | 17.51 |
| SK | 2.54 | 0.99 | 60.09 | 5.03 |
| CoK | 0.49 | 0.1 | 4.37 | 32.8 |
| BrK | 0.36 | 0.06 | 0.76 | 72.57 |

EXAMPLE 3

Testing Effect of pH on Catalyst

The porphyrin-based water splitting catalysts were also tested to determine their impact on the oxygen evolution reaction in acidic, neutral, and basic media. A glassy carbon electrode was prepared according to Examples 1-2. The weight loading of the catalyst on top of the base electrode was 2 mg cm$^{-2}$. Phosphate buffer solution, an aqueous mixture of 0.5 M potassium dihydrogen phosphate (KH$_2$PO$_4$) and 0.5M potassium hydrogen phosphate (K$_2$HPO$_4$) was used as medium. A neutral medium of pH 7 was obtained by mixing 21.0 ml of KH$_2$PO$_4$ with 30.0 ml of K$_2$HPO$_4$. An acidic solution of pH 1 was obtained by mixing 49.3 ml of KH$_2$PO$_4$ with 0.7 ml of K$_2$HPO$_4$. A basic solution of pH 13 was obtained by mixing 0.6 ml of KH$_2$PO$_4$ with 49.4 ml of K$_2$HPO$_4$ to produce a pH 8.85 buffer and adding sufficient NaOH to reach pH 13. Electrochemical measurements were performed using a conventional three-electrode cell and an Ezstat potentiostat/galvanostat supported by Ezstat software. The composite electrode was used as a working electrode. The counter electrode was made of a platinum mesh (area 1 cm$^2$). The reference electrode as Ag/AgCl/Kcl (sat.). Linear sweep voltammograms were recorded by scanning the potential of the working electrode at a scan rate of 100 mV s$^{-1}$ in a buffer solution of the required pH. The potential was measured against the Ag/AgCl/KCl (sat.), then was converted to a normal hydrogen electrode by adding 0.197 V.

Figure 5:
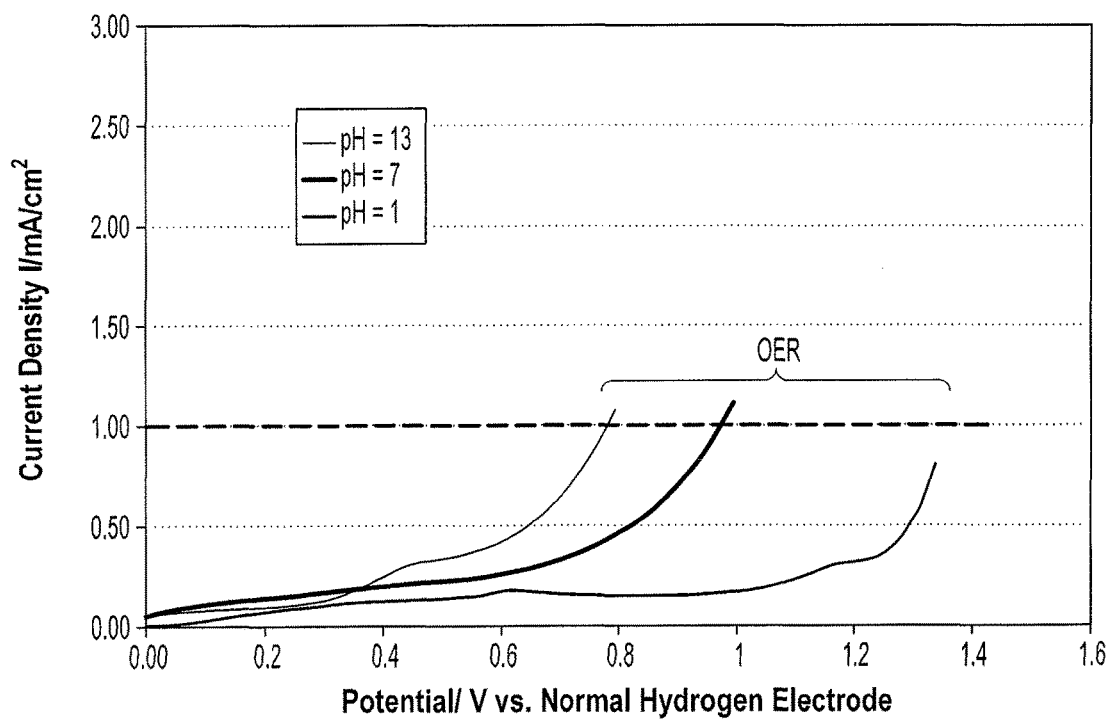
FIG. 5 depicts a graph of current density versus potential curves recorded from a porphyrin-based catalyst for water splitting coated electrode in solutions with varying pH.

FIG. 5 depicts a graph of current density versus potential curves recorded from solutions with pH=1, pH=7, and pH=13. The dashed line indicates the electrode potential corresponding to a current density of 1 mA cm$^{-2}$. The oxygen evolution reaction region is also highlighted. It is generally understood that the potential required to perform the oxygen evolution reaction increases as pH decreases.

It is to be understood that the porphyrin-based catalysts for water splitting is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A composite electrode, comprising:
 a glassy carbon electrode; and
 a porphyrin catalyst coated on the glassy carbon electrode;
 wherein the porphyrin catalyst comprises a composite having a mixture of:
 a porphyrin compound;
 conductive carbon; and
 a polymer binder selected from the group consisting of Nafion oil and polyvinylidene difluoride; and
 wherein the porphyrin compound has the formula:

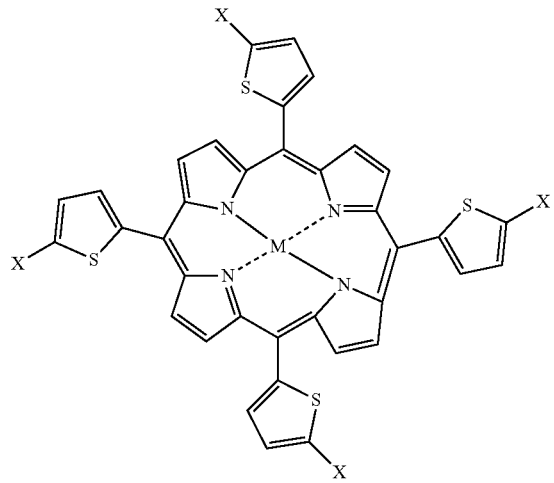

wherein M is H$_2$, Co, Ni, Cu, or Zn, and X is F, Cl, or Br.

2. The composite electrode according to claim 1, wherein the catalyst is active under pH conditions between pH 1 and pH 13.

3. A method of making a composite electrode according to claim 1 with a porphyrin catalyst for water splitting, comprising the steps of:
 dispersing the conductive carbon in an organic solvent to form a first reaction mixture;
 adding the porphyrin compound to the first reaction mixture to produce a second reaction mixture and mixing the second reaction mixture;
 adding a polymer solution comprising the polymer binder to the second reaction mixture to produce a third reaction mixture and mixing the third reaction mixture;
 coating the third reaction mixture onto the surface of the glassy carbon electrode; and
 drying the glassy carbon electrode.

4. The method of making a composite electrode of claim 3, wherein the dispersing and mixing steps comprise ultrasonic mixing using an ultrasonic probe for one hour.

* * * * *